US012746227B2

United States Patent

De Azevedo et al.

(10) Patent No.: US 12,746,227 B2
(45) Date of Patent: Sep. 29, 2026

(54) BENZIMIDAZOLE COMPOUND FOR THE TREATMENT OF METABOLIC DISORDERS

(71) Applicant: ACHÉ LABORATÓRIOS FARMACÊUTICOS S.A., Sao Paulo (BR)

(72) Inventors: Hatylas Felype Zaneti De Azevedo, Sao Paulo (BR); Marcos Antonio Ferreira Junior, Sao Paulo (BR); Natanael Dante Segretti, Guamlhos (BR); Alessandra Mascarello, Sao Paulo (BR); Cristiano Ruch Werneck Guimarães, Sao Paulo (BR)

(73) Assignee: ACHÉ LABORATÓRIOS FARMACÊUTICOS S.A., Sao Paulo (BR)

( * ) Notice: Subject to any disclaimer, the term of this patent is extended or adjusted under 35 U.S.C. 154(b) by 788 days.

(21) Appl. No.: 17/915,248

(22) PCT Filed: Apr. 15, 2021

(86) PCT No.: PCT/BR2021/050158

§ 371 (c)(1),
(2) Date: Sep. 28, 2022

(87) PCT Pub. No.: WO2021/207816

PCT Pub. Date: Oct. 21, 2021

(65) Prior Publication Data

US 2023/0128304 A1 Apr. 27, 2023

Related U.S. Application Data

(60) Provisional application No. 63/010,128, filed on Apr. 15, 2020.

(51) Int. Cl.
*A61K 31/4184* (2006.01)
*A61P 1/16* (2006.01)
*A61P 3/10* (2006.01)

(52) U.S. Cl.
CPC ............ *A61K 31/4184* (2013.01); *A61P 1/16* (2018.01); *A61P 3/10* (2018.01)

(58) Field of Classification Search
CPC .................................................. A61K 31/4184
See application file for complete search history.

(56) References Cited

U.S. PATENT DOCUMENTS 6,034,239 A * 3/2000 Ohkawa ............... C07D 491/04 564/189
6,124,463 A 9/2000 Beck et al.
(Continued)

FOREIGN PATENT DOCUMENTS

WO WO 2018076090 5/2018
WO WO-2018076090 A1 * 5/2018 ......... A61K 31/4184
WO WO 2019086744 5/2019

OTHER PUBLICATIONS

Hargens ((2013). Association between sleep disorders, obesity, and exercise: a review. Nature and Science of Sleep, 5, 27-35. https://doi.org/10.2147/NSS.S34838). (Year: 2013).*
(Continued)

*Primary Examiner* — Benjamin J Packard

(74) *Attorney, Agent, or Firm* — B. Aaron Schulman, Esq.; Stites & Harbison, PLLC

(57) ABSTRACT

The present invention broadly concerns a benzimidazole compound of formula (I) for the treatment of obesity, diabetes, non-alcoholic fatty liver disease and non-alcoholic steatohepatitis: Formula (I) or pharmaceutically acceptable salts, crystals, hydrates, prodrugs, metabolites, or solvates thereof.

4 Claims, 3 Drawing Sheets

(56) References Cited

U.S. PATENT DOCUMENTS

| | | | |
|---|---|---|---|
| 8,394,969 | B2 | 3/2013 | Bookser et al. |
| 10,781,182 | B2 | 9/2020 | Ruch Werneck Guimarãs et al. |
| 11,091,445 | B2 | 8/2021 | Ruch Werneck Guimarãs et al. |
| 2005/0014812 | A1 | 1/2005 | Hayashida et al. |
| 2010/0081643 | A1 | 4/2010 | Bookser et al. |
| 2011/0112148 | A1 | 5/2011 | Falco et al. |
| 2019/0270711 | A1 | 9/2019 | Ruch Werneck Guimarãs et al. |
| 2020/0277265 | A1 | 9/2020 | Ruch Werneck Guimarãs et al. |

OTHER PUBLICATIONS

International Search Report for PCT/BR2021/050158 dated Aug. 10, 2021.

Written Opinion of the International Searching Authority for PCT/BR2021/050158 dated Aug. 10, 2021.

Karamitri, et al., "Melatonin in type 2 diabetes mellitus and obesity", Nature Reviews | Endocrinology, vol. 15, (Feb. 2019), pp. 105.

Extended European Search Report dated Apr. 17, 2024 in European Patent Application No. 21788866.8.

Laudon, et al, "Therapeutic Effects of Melatonin Receptor Agonists on Sleep and Comorbid Disorders", Sep. 9, 2014, pp. 15924-15950, vol. 15, Int. J. Mol. Sci., XP055688381.

Meihua, et al, "Melatonin receptors in diabetes: A potential new therapeutical target?", Dec. 1, 2014, pp. 220-223, vol. 744, European Journal of Pharmacology, XP093144531.

Karamitri, et al, "Melatonin in type 2 diabetes mellitus and obesity", Dec. 7, 2018, pp. 105-125, vol. 15, No. 2, Nature Reviews, XP036705979.

* cited by examiner

[Fig. 1]
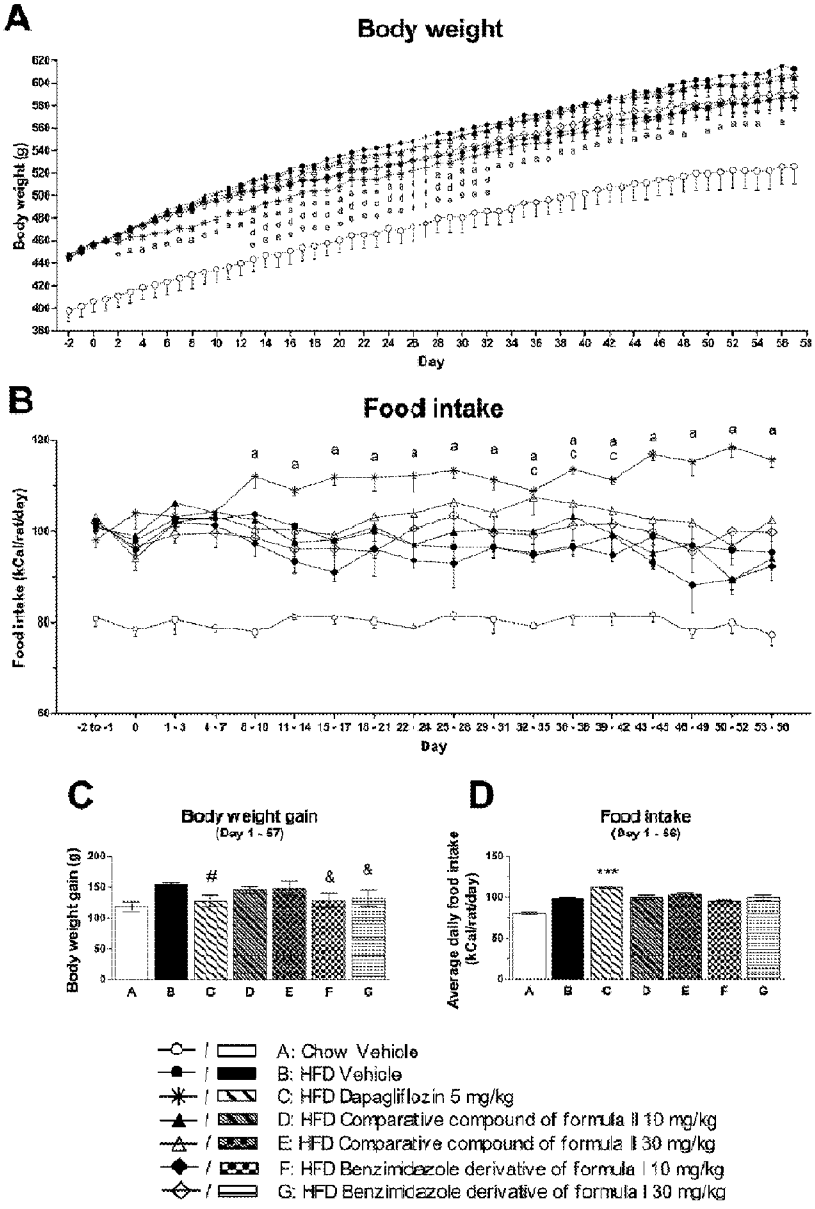

[Fig. 2]
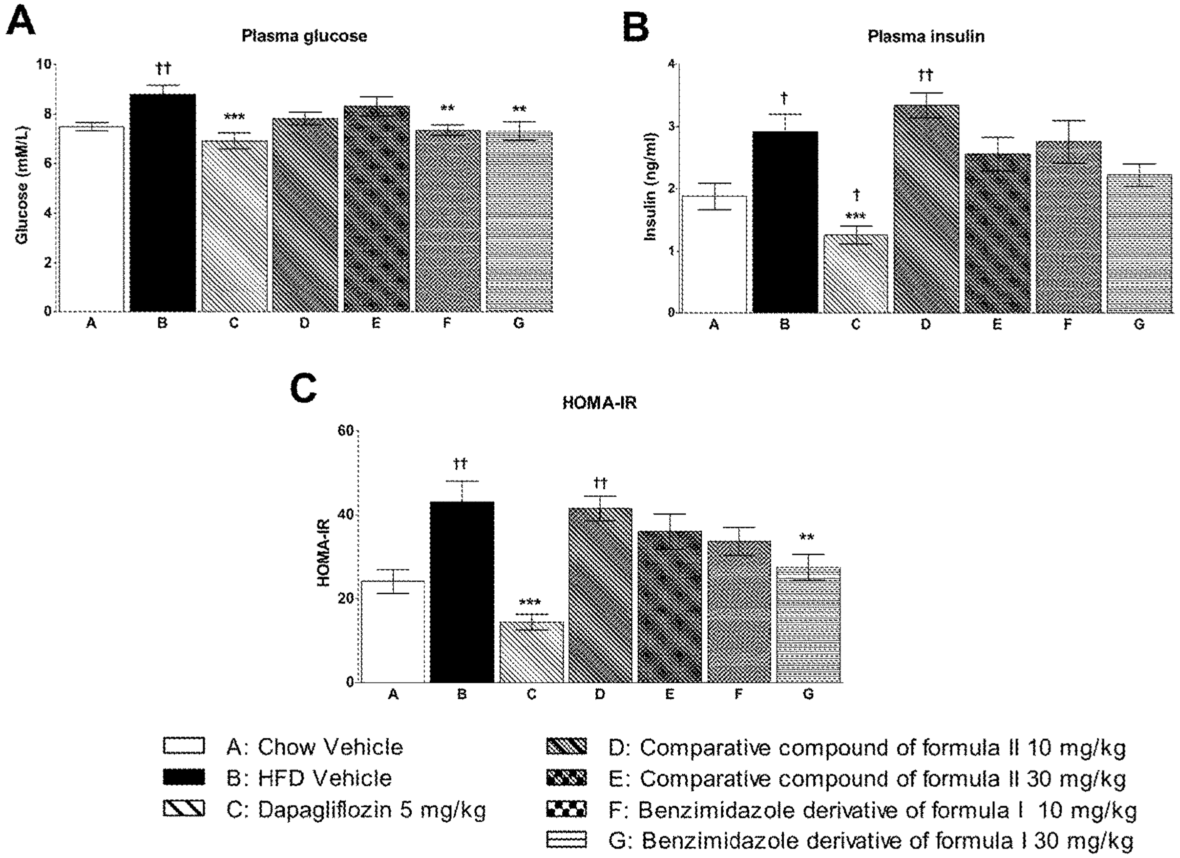

[Fig. 3]
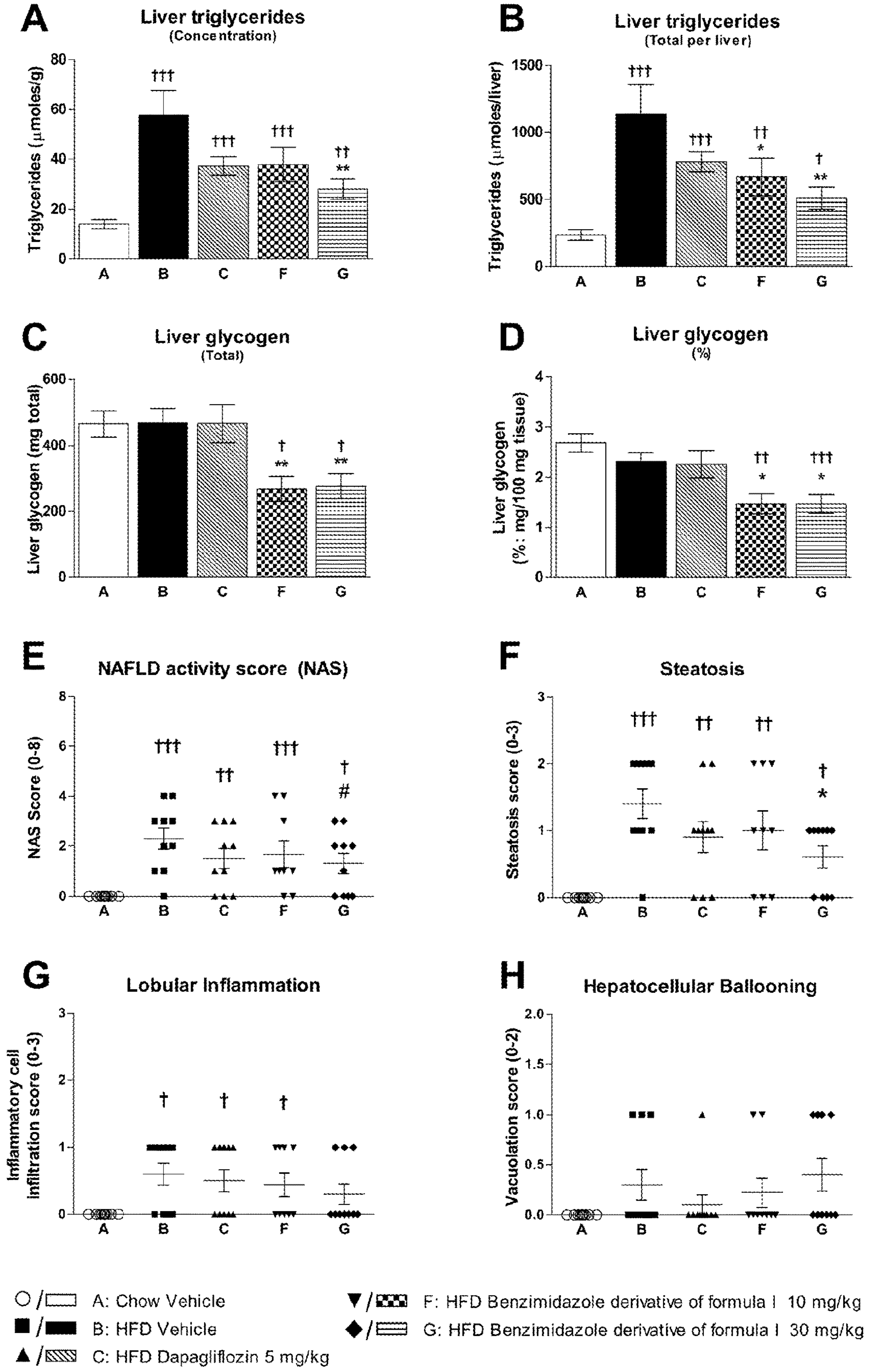

BENZIMIDAZOLE COMPOUND FOR THE TREATMENT OF METABOLIC DISORDERS

FIELD OF THE INVENTION

The present invention broadly concerns a benzimidazole compound for the treatment of obesity, diabetes, non-alcoholic fatty liver disease and non-alcoholic steatohepatitis.

PRIOR ART

Obesity, diabetes and non-alcoholic fatty liver disease (NAFLD) have become major public health issues worldwide and the scale of these epidemics continues to rise annually. Obesity is a chronic condition that represents a major risk factor for the development of several comorbidities, such as diabetes and NAFLD (Wang C and Liao J K (2013). A Mouse Model of Diet-Induced Obesity and Insulin Resistance. Methods Mol Biol. 821: 421-433). According to the World Health Organization (WHO) estimative, there were more than 1.9 billion overweight adults globally in 2016, of which 650 million were obese. The global prevalence of NAFLD is estimated at 25% of the world population. However, an even higher prevalence, 42% to 70%, is observed in diabetic patients. Moreover, 1 in 11 adults are expected to have diabetes mellitus.

NAFLD is a complex disease that can be classified as non-alcoholic fatty liver (NAFL) and non-alcoholic steatohepatitis (NASH), depending on its severity. NAFL consists of hepatic steatosis without significant hepatocellular injury, while NASH is characterized by a combination of steatosis, hepatocyte damage and inflammation with or without fibrosis. NAFLD may further progress to cirrhosis, hepatocellular carcinoma and other complications for which liver transplantation is the only therapeutic option. There are currently no approved drugs in the market for the treatment of NAFLD. Given the high level of unmet clinical need in the area, the development of novel therapies for the treatment of obesity, diabetes, NAFLD and NASH is of significant interest.

Melatonin (N-acetyl-5-methoxytryptamine) is a natural hormone that influences the circadian regulation of glucose and insulin levels, synchronizing the metabolism with the daily feeding and fasting cycle (Cipolla-Neto J et al. (2014). Melatonin, energy metabolism, and obesity: a review. J Pineal Res. 56(4):371-81). Genetic mutations in melatonin receptors and altered melatonin signaling have been related to increased fasting plasma glucose levels, impaired insulin secretion and higher risk of type 2 diabetes (Bouatia-Naji N et al. (2009). A variant near MTNR1B is associated with increased fasting plasma glucose levels and type 2 diabetes risk. Nat Genet. 41(1):89-94; Tuomi T et al. (2016). Increased Melatonin Signaling Is a Risk Factor for Type 2 Diabetes. Cell Metab. 23(6):1067-1077). Studies in mice genetically ablated for MT1 (MT1−/−) or MT2 (MT2−/−) have shown different effects of these receptors on glucose and insulin metabolism. MT1−/− mice exhibit a robust metabolic phenotype, with higher cumulative weight gain, hyperglycemia and marked insulin resistance. In contrast, MT2−/− mice have reduced hepatic insulin sensitivity but increased insulin release (Owino S et al. (2018). Nocturnal activation of melatonin receptor type 1 signaling modulates diurnal insulin sensitivity via regulation of PI3K activity. J Pineal Res. 64(3); Tuomi T et al. (2016). Increased Melatonin Signaling Is a Risk Factor for Type 2 Diabetes. Cell Metab. 23(6):1067-1077). Moreover, the regulation of MT1 and MT2 has important differences upon melatonin stimulation. The activation of MT2 desensitizes cAMP response, whereas activation of MT1 leads to cAMP supersensitization in the subsequent withdrawal period (Witt-Enderby P A et al. (1998). Physiological exposure to melatonin supersensitizes the cyclic adenosine 3',5'-monophosphate-dependent signal transduction cascade in Chinese hamster ovary cells expressing the human mt1 melatonin receptor. Endocrinology. 139(7):3064-71; Karamitri A et al. (2019). Melatonin in type 2 diabetes mellitus and obesity. Nat Rev Endocrinol. 15(2):105-125). Although these findings suggest that drugs that regulate MT1/MT2 receptors could have a positive impact in the treatment of obesity, diabetes and liver metabolic diseases, drugs targeting specific melatonin receptors (MT1 or MT2) in peripheral tissues have never been developed.

SUMMARY OF THE INVENTION

The present invention broadly concerns a benzimidazole compound of formula I for the treatment of obesity, diabetes, non-alcoholic fatty liver disease and non-alcoholic steatohepatitis:

[Chem.1]

Formula I

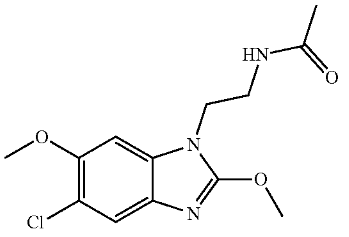

or pharmaceutically acceptable salts, crystals, hydrates, prodrugs, metabolites or solvates thereof.

Within the meaning of the benzimidazole derivate compound of the invention are also included pharmaceutically acceptable salts, crystals, hydrates and solvates thereof, provided they significantly afford activity of the compound. Within the meaning of the benzimidazole derivate compound of the invention are also included prodrugs and metabolites thereof, as well as the free base molecule with minor modifications (e.g. inclusion of substituents), which, as known to a person having skill in the art, result in equivalent compounds and do not significantly modify the pharmacophore of the molecule towards treatment of obesity, diabetes, non-alcoholic fatty liver disease and non-alcoholic steatohepatitis.

Another aspect of the invention are pharmaceutically acceptable acid addition salts of the compound of formula I, such as inorganic addition salts e.g. hydrochloride, hydrobromide, sulfate, nitrate, phosphate, and pharmaceutically acceptable organic additions salts of the compound of formula I such as acetate, propionate, hexanoate, heptanoate, glycolate, piruvate, lactate, malonate, malate, maleate, fumarate, tartrate, citrate, succinate, mesylate, acistrate, besylate, tosylate, xinafoate, benzoate, p-toluenesulfonate, cinnamate, p-chlorobenzenesulfonate, 2-naphtalenesulfonate, p-toluenesulphonate, camphorsulfonate, trimethylacetate, t-butylacetate, laurylsulphate, gluconate, glutarate, hydroxynaphthoate, salicylate, stearate, muconate, mandelate, 2-hydroxyethanesulfonate and from the alkaline addition salts of metals sodium, potassium, lithium, calcium, magnesium, bismuth, bromide; and from or pharmaceutically acceptable salts with the organic bases primary, secondary or tertiary amines; and salts with the aminoacid arginine, lysine, histidine, caffeine, procaine, hydrobamine, choline, betaine, ethylenediamine, glycosamine, teobromine, purine, morpholine.

The present invention also refers to a pharmaceutical composition for the treatment of obesity, diabetes, non-alcoholic fatty liver disease and non-alcoholic steatohepatitis comprising the compound of formula I and pharmaceutical acceptable excipients.

The selection of excipients to be used or preparing pharmaceutical compositions is generally undertaken by considering the type of administration pathway, the physical and chemical compatibility of the excipient with the active ingredient, the manner of preparing the pharmaceutical presentation and the effects on its efficacy. These excipients are known in the art and are described in the literature (for instance in: Handbook of Pharmaceutical Manufacturing Formulations—Vol. 1 a 6-2004 Sarfaraz K. Niazi—CRC Press and Remington's Pharmaceutical Sciences, Mack Publishing), widely used by technical professionals in the matter.

For therapeutic use and administration, the benzimidazole compound of the present invention may be formulated in compositions appropriate for oral, parenteral, nasal, rectal, transmucosal and transdermal administration, using conventional techniques and appropriate excipients.

There are no specific restrictions as to the dosage forms comprising the benzimidazole compound of the invention. For instance, as a solid for oral administration adequate dosage forms may be tablets, pills, dragées, capsules, granules, powders, pellets, lyophilizates and similar presentations. As a liquid for oral administration, adequate dosage forms may be solutions, dispersions, suspensions, emulsions, oils, syrups, etc. Liquid dosage forms may be used for injections, such as intravenous, intramuscular, subcutaneous and intradermal.

Other examples of dosage forms comprise liposomes and nanoparticles, or any other known administration aspects to a person skilled in the art. The dosage form may provide immediate, controlled or delayed release of the benzimidazole compound of the invention.

In other embodiments, the present invention refers the use of the compound of formula I in the manufacture of pharmaceutical composition for the treatment of obesity, diabetes, non-alcoholic fatty liver disease and non-alcoholic steatohepatitis.

Another aspect of the invention are dosage forms, as described above, containing 0.01 a 5000 mg of the benzimidazole compound of the invention, for example, and may be administered once or more times a day, during the treatment.

In a particular embodiment, the composition of the invention may comprise, other than the benzimidazole compound, at least another active principle used for the treatment of obesity, diabetes, non-alcoholic fatty liver disease and non-alcoholic steatohepatitis, for instance chosen from metformin, insulin and derivatives thereof, sulphonylureas, SGLT-2 inhibitors, DPP4 inhibitors, GLP-1 agonists, meglitinides, thiazolidinediones, alpha-glucosidase inhibitors, FXR agonist, PPAR agonists, ASK1 inhibitor, CCR2 and CCR5 antagonists, caspase inhibitors, insulin sensitizers and cholic-arachidic acid conjugates.

In another aspect, the invention concerns the Method for the treatment of obesity, diabetes, non-alcoholic fatty liver disease and non-alcoholic steatohepatitis comprising a benzimidazole compound of formula I:

[Chem.2]

Formula I

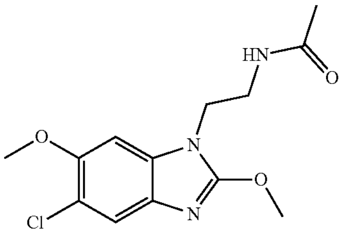

or pharmaceutically acceptable salts, crystals, hydrates, solvates, prodrugs or metabolites thereof.

BRIEF DESCRIPTION OF THE DRAWINGS

FIG. 1 A to D show the effect of the compound of formula I on body weight (BW) and food intake (FI) of male SD rats maintained on HFD. The benzimidazole compound of formula I, the comparative compound of formula II, and dapagliflozin were administered to animals fed HFD. Vehicle was administered to animals fed normal chow or HFD. Data is shown as adjusted means—SEM of n=9-10 animals (BW and BW gain) or n=5 cages (FI and average daily FI) per group. Data was analyzed by ANCOVA with BW on day 1 (A and C) or average FI during the baseline period (B and D) as covariate, excluding the Chow Vehicle group. Treatment groups were compared with HFD Vehicle by separate Williams' tests (compounds I or II) or multiple t tests (dapagliflozin) and considered statistically significant if $p<0.05$. Statistical significance is denoted as "a", "b", "c", "d" and "e" for HFD groups treated respectively with dapagliflozin, compound II at 10 mg/kg, compound II at 30 mg/kg, compound I at 10 mg/kg and compound I at 30 mg/kg. # ($p=0.051$) and & ($p=0.098$) mean trends toward significance in comparisons with HFD Vehicle.

FIG. 2 A to C show the effect of the compound of formula I on plasma glucose (A), insulin (B) and HOMA-IR (C) of male SD rats maintained on HFD. Compound I, compound II, dapagliflozin were administered to animals fed HFD. Vehicle was administered to animals fed normal chow or HFD. The parameters were assessed on day 51. Data is displayed as adjusted means±SEM (n=9-10). The statistical analysis was done using general linear model (glucose and HOMA-IR) or robust regression (insulin) of log transformed data (insulin), with treatment as factor and bleeding orders and BW on day 1 (except comparisons against the Chow Vehicle group) as covariates. Treatment groups were compared with HFD Vehicle by separate Williams' tests (compound II and compound I) or multiple t tests (dapagliflozin) and statistically significant differences are denoted by $p<0.01$ and *$p<0.001$. Comparisons against Chow Vehicle were performed by multiple t tests (HFD Vehicle and dapagliflozin groups) or Dunnett's test (compound I and compound II) and statistically significant differences are denoted by † ($p<0.05$) and †† ($p<0.01$).

FIG. 3 A to H show the effect of the compound of formula I on liver triglycerides (A-B), glycogen (C-D) and histopathology (E-H) of male SD rats maintained on HFD. The parameters were assessed following a chronic oral treatment with compound I at 10 and 30 mg/kg, dapagliflozin at 5 mg/kg, or vehicle to animals receiving HFD. Vehicle was also administered to animals receiving normal chow. The liver triglycerides were quantified using Cobas C111 clinical analyzer TRIGL 04657594 190. Glycogen quantification in liver samples was performed using commercial kits (Thermo BioVision, Glycogen Assay Kit, K646-100). Data is shown as means±SEM (A-D) or raw data including mean±SEM (E-H), n=9-10. The statistical analysis of liver triglycerides (A-B) and glycogen (C-D) was performed by general linear model of log transformed data (triglycerides only) with treatment and cohort as factors and termination order and BW on day 1 as covariates. Treatment groups were compared with HFD Vehicle by separate Williams' tests (compound I) or multiple t tests (dapagliflozin) and statistically significant differences are denoted by * ($p<0.05$),  ($p<0.01$) and * ($p<0.001$). Comparisons against Chow Vehicle were performed by multiple t tests (HFD Vehicle and dapagliflozin groups) or Dunnett's test (compound I) and statistically significant differences are denoted by † ($p<0.05$), †† ($p<0.01$) and ††† ($p<0.001$). Analysis of liver histopathology data (E-H) was done by exact Wilcoxon rank sum test. Statistical differences are denoted by * ($p<0.05$) in comparison with HFD Vehicle and by † ($p<0.05$), †† ($p<0.01$) and ††† ($p<0.001$) when compared with Chow Vehicle.

DESCRIPTION OF THE INVENTION

A research investigation found a certain benzimidazole derivative of formula I, which is also named N-[2-(5-Chloro-2,6-dimethoxy-benzoimidazol-1-yl)-ethyl]-acetamide:

[Chem.3]

Formula I

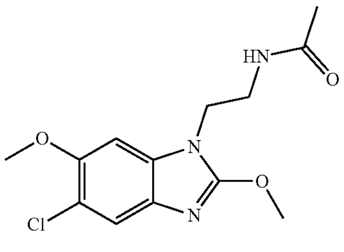

or pharmaceutically acceptable salts, crystals, hydrates, prodrugs, metabolites or solvates thereof.

1H NMR (400 MHz $CDCl_3$) δ 1.91 (s, 3H), 3.52-3.57 (m, 2H), 3.91 (s, 3H), 4.10-4.14 (m, 5H), 5.62 (br s, 1H), 6.80 (s, 1H), 7.52 (s, 1H). $^{13}C$ NMR (125 MHz, CDCl3) δ ppm 23.16; 39.00; 41.16; 56.94; 57.21; 93.02; 116.73; 119.08; 133.20; 133.68; 150.85; 157.61; 170.81. MS (ESI) m/z calculated $C_{13}H_{16}ClN_3O_3$: 297.0880; found $[M+H]^+$ 298.0977.

This compound was invented to act as a i) melatonergic agonist with higher potency at MT1 than at MT2 receptor (Table 1) and to ii) exhibit higher peripheral than central exposure, i.e., low brain-to-plasma ratio (Table 2), thus acting preferentially on peripheral tissues. The benzimidazole derivative of formula I according to the present invention is a potent, peripherally-preferred melatonin receptor agonist, with moderate selectivity toward the MT1 receptor, that regulates weight gain and insulin resistance, liver triglyceride levels and histology-determined steatosis. Thus, the benzimidazole derivative of formula I according to the present invention adds significant value to the treatment of obesity, diabetes and NAFLD/NASH.

Therefore, the present invention concerns a benzimidazole compound of formula I for the treatment of obesity, diabetes, non-alcoholic fatty liver disease and non-alcoholic steatohepatitis:

[Chem.4]

Formula I

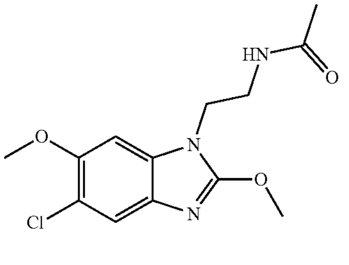

or pharmaceutically acceptable salts, crystals, hydrates, prodrugs, metabolites or solvates thereof.

Within the meaning of the benzimidazole derivate compound of the invention are also included pharmaceutically acceptable salts, crystals, hydrates and solvates thereof, provided they significantly afford activity of the compound. Within the meaning of the benzimidazole derivate compound of the invention are also included prodrugs and metabolites thereof, as well as the free base molecule with minor modifications (e.g. inclusion of substituents), which, as known to a person having skill in the art, result in equivalent compounds and do not significantly modify the pharmacophore of the molecule towards treatment of obesity, diabetes, non-alcoholic fatty liver disease and non-alcoholic steatohepatitis.

Without excluding any other alternatives, adequate salts of the benzimidazole compound of the invention are pharmaceutically acceptable acid addition salts thereof, such as inorganic addition salts e.g. hydrochloride, hydrobromide, sulfate, nitrate, phosphate, and pharmaceutically acceptable organic additions salts such as acetate, propionate, hexanoate, heptanoate, glycolate, piruvate, lactate, malonate, malate, maleate, fumarate, tartrate, citrate, succinate, mesylate, acistrate, besylate, tosylate, xinafoate, benzoate, p-toluenesulfonate, cinnamate, p-chlorobenzenesulfonate, 2-naphtalenesulfonate, p-toluenesulphonate, camphorsulfonate, trimethylacetate, t-butylacetate, laurylsulphate, gluconate, glutarate, hydroxynaphthoate, salicylate, stearate, muconate, mandelate, 2-hydroxyethanesulfonate and from the alkaline addition salts of metals sodium, potassium, lithium, calcium, magnesium, bismuth, bromide; and from or pharmaceutically acceptable salts with the organic bases primary, secondary or tertiary amines; and salts with the aminoacid arginine, lysine, histidine, caffeine, procaine, hydrobamine, choline, betaine, ethylenediamine, glycosamine, teobromine, purine, morpholine.

The present invention also refers to a pharmaceutical composition for the treatment of obesity, diabetes, non-alcoholic fatty liver disease and non-alcoholic steatohepatitis comprising the compound of formula I and pharmaceutical acceptable excipients.

The selection of excipients to be used or preparing pharmaceutical compositions is generally undertaken by considering the type of administration pathway, the physical and chemical compatibility of the excipient with the active ingredient, the manner of preparing the pharmaceutical presentation and the effects on its efficacy. These excipients are known in the art and are described in the literature (for instance in: Handbook of Pharmaceutical Manufacturing Formulations—Vol. 1 a 6—2004—Sarfaraz K. Niazi—CRC Press and Remington's Pharmaceutical Sciences, Mack Publishing), widely used by technical professionals in the matter.

Pharmaceutical excipients usually classified or sub-classified on the basis of the function that they perform in the pharmaceutical compositions and/or in their manufacturing technique. They may be called diluting agents, binding agents, breakdown or anti-clumping agents, lubricants, suspension agents, thickening agents, solvents, surfactants, slip agents, anti-clumping or flow agents, coating agents, plastifying agents, sweeteners, isotonicity agents, colorants, conservants, antioxidants, pH control or modification agents, complexing agents used to mask flavor, improve solubility, promote formulation stability, and modulate bioavailability, in addition to chelating, aromatizing and flavorizing agents.

Diluting agents are pharmaceutical excipients included in solid dosage forms, such as tablets, capsules, pills, pellets, powders and granules, in order to increase the volume or the weight of the type of dosage. They also may be used in liquid and semi-solid pharmaceutical forms for the same purpose. Examples of diluting agents appropriate for the preparation of pharmaceutical compositions of this invention include but are not limited to: calcium carbonate, calcium phosphates, calcium sulfate, microcrystal cellulose, powdered cellulose, dextrins, dextrose, fructose, kaolin, anhydrous and/or monohydrated lactose, maltose, sorbitol, assorted starches (maize, wheat, potato, tapioca), pre-gelatinized starch, saccharose and sugar.

Binding agents are pharmaceutical excipients that are included in the formulations in order to ensure easier clumping of powders into granules during the blending (or granulation) stage, using water as a granulation fluid, or hydro-alcohol mixtures or other solvents. Binding agents may also be used in dry blending processes where no fluids are required. Examples of binding agents appropriate for the preparation of the pharmaceutical composition of this invention include but are not limited to: acacia gum, alginic acid, ammonium methacrylate copolymer, carbomer copolymer or homopolymer or interpolymer, starches (maize, wheat, potato, tapioca), microcrystal cellulose, methyl cellulose, ethyl cellulose, hydroxypropylmethyl cellulose, dextrin, maltodextrin, maltose, saccharose, gelatin, glucose, guar gum and povidone.

Breakdown or anti-clumping agents are pharmaceutical excipients that can speed up the breakdown or dissolution of the formulation when in contact with biological fluids. Examples of breakdown or anti-clumping agents appropriate for the preparation of the pharmaceutical composition of this invention include but are not limited to: alginic acid, starches, sodium alginate, sodium croscaramelose, sodium glycolate, sodium carboxymethyl cellulose, microcrystal cellulose and crospovidone.

Lubricants are excipients that reduce friction among the particles in the formulations and also lessen the friction between the particles and the walls of the equipment used to prepare them. Examples of lubricants appropriate for the preparation of the pharmaceutical composition of this invention include but are not limited to: calcium stearate, magnesium stearate, zinc stearate, mineral oil, polyethylene glycol, sodium lauryl sulfate, sodium stearyl fumarate, starch, stearic acid, talc and type I hydrogenated vegetable oil.

Suspension agents and thickening agents are excipients used in formulations to ensure the stability of dispersed systems (for example, suspensions and emulsions), in order to reduce particle sedimentation speed or to lessen the fluidity of liquid formulations. Examples of appropriate suspension agents and thickening agents for preparing the pharmaceutical composition of this invention include but are not limited to: acacia gum, agar, alginic acid, aluminum monostearate, bentonite, carbomer, copolymer carbomer, homopolymer carbomer, interpolymer carbomer, cálcium or sodium carboxymethyl cellulose, carrageenan, microcrystal cellulose, dextrin, guar gum, gellan gum, hydroxyethyl cellulose, hydroxypropylcellulose, methyl cellulose, aluminum magnesium silicate, pectin, polyethylene oxide, polyvinyl alcohol, povidone, propylene glycol alginate, sodium alginate, silicon dioxide, colloidal silicon dioxide, starches (maize wheat, potato, tapioca), tragacanth gum and xanthan gum.

Solvents are excipients employed to dissolve other substances when preparing liquid, semi-solid and solid compositions, used for the latter in order to ensure easier blending and/or to provide a blend with a homogeneous concentration of the active pharmaceutical ingredient or some other excipient. Examples of solvents appropriate for the preparation of the pharmaceutical composition of this invention include but are not limited to: water, ethanol, isopropanol, plant oils (maize, cotton, sesame, soy), mineral oil, glycerin, sorbitol and oleic acid.

Surfactants are also known as surface tension modulation agents, and are excipients with assorted functions, used as emulsifiers, humectants and/or solubilization agents. Examples of surfactants appropriate for the preparation of the pharmaceutical composition of this invention include but are not limited to: benzalkonium chloride, benzethonium chloride, cetylpyridinium chloride, nonoxynol 9, octoxynol 9, polyoxyl 50 stearate, polyoxyl 10 oleyl ether, polyoxyl 20 cetostearyl ether, polyoxalate 35 ricin oil, hydrogenated polyoxalate 40 ricin oil, polyoxyl 40 stearate, polyoxyl lauryl ether, polyoxyl stearyl ether, polysorbate 20, polysorbate 40, polysorbate 60, polysorbate 80, sodium cetoestearyl sulfate, sodium lauryl sulfate, sorbitan monolaurate, sorbitan monoleate, sorbitan monoplamitate, sorbitan sesquioleate, sorbitan trioleate, cetyl alcohol, oleyl alcohol, poloxamer, propylene glycol monostearate, carbomer copolymer or interpolymer, cholesterol, monoethanolamine, diethanolamine, triethanolamine, diethylene glycol stearates, sodium docusate, ethylene glycol stearates, glyceryl distearates, glyceryl monolinoleate, glyceryl monooleate, glyceryl monostearate, lanolin alcohols, lecithin, mono and diglycerides, sodium stearate, stearic acid and emulsifying wax.

Flow agents, anti-clumping or slip agents are excipients used in formulations to promote flows and reduce clumping in solids conduction funnels during powder flows and processing. Examples of flow agents, anti-clumping or slip agents appropriate for the preparation of the pharmaceutical composition of this invention include but are not limited to: calcium silicate, magnesium silicate, colloidal silicon dioxide and talc.

Coating agents are excipients that may be used with various functions, including masking unpleasant flavors or odors, controlling drug release speed, enhancing appearance, easier swallowing and controlling the release of the drug in the digestive tract (for example enteric coating). Examples of coating agents appropriate for the preparation of the pharmaceutical composition of this invention include but are not limited to: ammonium methacrylate copolymer, sodium carboxymethyl cellulose, cellulose acetate phthalate, cellulose acetate, copovidone, ethyl cellulose and its aqueous dispersions, gelatin, pharmaceutical varnishes, hydroxypropyl cellulose, hydroxypropylmethyl cellulose, hydroxypropyl methylcellulose acetate succinate, hydroxypropylmethyl cellulose phthalate, maltodextrin, methacrylic acid copolymer and its dispersions, methyl cellulose, polyethylene glycol, polyvinyl acetate phthalate, shellac, modified pre-gelatinized starch, saccharose, titanium dioxide, carnauba wax and microcrystal wax.

Plastifying agents are excipients added to other agents in order to endow them with greater plasticity and resilience (elasticity). They are important components for conferring the physical properties required by polymer systems. Examples of plastifying agents appropriate for the preparation of the pharmaceutical composition of this invention include but are not limited to: acetyl tributyl citrate, acetyl triethyl citrate, ricin oil, diacetylated monoglycerides, dibutyl sebacate, sorbitol, dextrin, diethyl phthalate, glycerin, polyethylene glycol, polyethylene glycol monomethyl ether, propylene glycol, benzyl benzoate, triacetin, tributyl citrate, triethyl citrate and chlorobutanol.

For parenteral administration, it is normal to use isotonic solutions, meaning solutions with osmotic pressure similar to the tissues with which they come into contact, in order to avoid hemolyses, reducing pain and the discomfort of administration. Examples of isotonicity agents frequently used to ensure the isotonicity of the pharmaceutical composition of this invention include but are not limited to: dextrose, glycerin, manitol, sodium chloride, and potassium chloride.

Sweeteners are agents used to mask unpleasant flavors and sweeten oral formulations. Examples of sweeteners appropriate for the preparation of the pharmaceutical composition of this invention include but are not limited to: acesulfame potassium, aspartame, acesulfame aspartame salt, dextrates, dextrose, fructose, galactose, maltitol, maltose, manitol, saccharine, cálcium saccharine, sodium saccharine, sorbitol, sucralose, saccharose, sugar and tagatose.

The scope of the composition addressed by this invention also encompasses pharmaceutical colorants that are included in the dosing forms, in order to endow each medication with a distinct appearance, ensuring that it is easy to distinguish a specific formulation among formulations with similar physical aspects. Examples of pharmaceutical colorants appropriate for use in the composition of this invention include: red ferric oxide, yellow ferric oxide, ferric oxide blends, caramel, titanium dioxide, FD&C colorants and D&C colorants.

Depending on the administration pathway and the physical and chemical properties inherent to the compounds addressed by this invention, substances may be added to the pharmaceutical composition prepared with these compounds that can stabilize, preserve, prevent and/or avoid the premature degradation of its ingredients. These additional excipients may act as antioxidants, preservatives, pH regulators or modifiers. Examples of excipients used with these properties that are appropriate for the preparation of the pharmaceutical composition addressed by this invention include but are not limited to: ascorbic acid, sorbic acid, sodium meta bisulfite, alpha-tocopherol, methylparaben, propylparaben, butylparaben, sodium sulfite, butylated hydroxytoluene (BHT), butylated hydroxyanisole (BHA), phenol, benzyl alcohol, benzalkonium chloride, benzethonium chloride, cetylpyridinium chloride, benzoic acid, sodium benzoate, sodium propionate, boric acid and the pH control agents, the latter encompassing organic and inorganic acids, basis and buffers and normally used in pharmaceutical compositions.

The pharmaceutical composition encompassing the compounds addressed by this invention may also contain substances or be prepared with: (a) complexing agents to mask flavor, improve solubility, promote the solubility of the formulation and/or modulate bioavailability, and (b) aromatizing and flavorizing agents used to correct or mask unpleasant odors and flavors, or to confer pleasant odors and flavors. Several substances and preparations are available on the market for such applications, with their use being limited to approved agents, or those that have been duly certified, which are compatible with the ingredients in the composition. For therapeutic use and administration, the benzimidazole compound of the present invention may be formulated in compositions appropriate for oral, parenteral, nasal, rectal, transmucosal and transdermal administration, using conventional techniques and appropriate excipients.

There are no specific restrictions as to the dosage forms comprising the benzimidazole compound of the invention. For instance, as a solid for oral administration adequate dosage forms may be tablets, pills, dragées, capsules, granules, powders, pellets, lyophilizates and similar presentations. As a liquid for oral administration, adequate dosage forms may be solutions, dispersions, suspensions, emulsions, oils, syrups, etc. Liquid dosage forms may be used for injections, such as intravenous, intramuscular, subcutaneous and intradermal.

Other examples of dosage forms comprise liposomes and nanoparticles, or any other known administration aspects to a person skilled in the art. The dosage form may provide immediate, controlled or delayed release of the benzimidazole compound of the invention.

Another aspect of the invention are dosage forms, as described above, containing 0.01 a 5000 mg of the benzimidazole compound of the invention, for example, and may be administered once or more times a day, during the treatment.

In a particular embodiment, the composition of the invention may comprise, other than the benzimidazole compound, at least another active principle used for the treatment of obesity, diabetes, non-alcoholic fatty liver disease and non-alcoholic steatohepatitis, for instance chosen from metformin, insulin and derivatives thereof, sulphonylureas, SGLT-2 inhibitors, DPP4 inhibitors, GLP-1 agonists, meglitinides, thiazolidinediones, alpha-glucosidase inhibitors, FXR agonist, PPAR agonists, ASK1 inhibitor, CCR2 and CCR5 antagonists, caspase inhibitors, insulin sensitizers and cholic-arachidic acid conjugates.

In other embodiments, the present invention refers to the use of the compound of formula I i) in the manufacture of a pharmaceutical composition or ii) in the treatment of obesity, diabetes, non-alcoholic fatty liver disease and non-alcoholic steatohepatitis.

In another aspect, the invention concerns the method for the treatment of obesity, diabetes, non-alcoholic fatty liver disease and non-alcoholic steatohepatitis comprising a benzimidazole compound of formula I:

[Chem.5]

Formula I

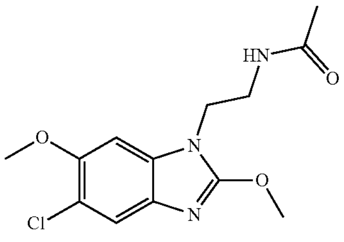

or pharmaceutically acceptable salts, crystals, hydrates, solvates, prodrugs or metabolites thereof.

Non-exhaustive examples are presented below to show effects of benzimidazole derivative of formula I of the present invention.

EXAMPLES

Example 1—Effects of Benzimidazole Derivative of Formula I

The effects of benzimidazole derivative of formula I were assessed in Sprague Dawley (SD) rats maintained on a high fat diet (HFD), which represents a diet-induced obesity (DIO) model that exhibits alterations similar to obesity, diabetes and non-alcoholic fatty liver disease (NAFLD) in humans, such as insulin resistance and triglycerides accumulation in the liver (van Herck M A et al. (2017). Animal Models of Nonalcoholic Fatty Liver Disease-A Starter's Guide. Nutrients. 9(10). pii: E1072; Wang C and Liao J K (2013). A Mouse Model of Diet-Induced Obesity and Insulin Resistance. Methods Mol Biol. 821: 421-433). The effects of the benzimidazole derivative of formula I, a more potent agonist at MT1 than MT2, were compared to N-[3-(5-Chloro-2-ethoxy-6-methoxy-benzoimidazol-1-yl)-propyl]-acetamide (structure depicted below—formula II), a melatonergic agonist with higher potency at MT2 than MT1 receptors (i.e., opposite of the benzimidazole derivative of formula I according to the present invention), and to those of dapagliflozin, a SGLT2 inhibitor that normalizes blood glucose levels and reduces body weight in DIO models (Millar P et al. (2017). Metabolic and neuroprotective effects of dapagliflozin and liraglutide in diabetic mice. J Endocrinol. 234(3):255-267; Devenny J J et al. (2012). Weight loss induced by chronic dapagliflozin treatment is attenuated by compensatory hyperphagia in diet-induced obese (DIO) rats. Obesity. 20: 1645-1652.).

[Chem.6]

Formula I

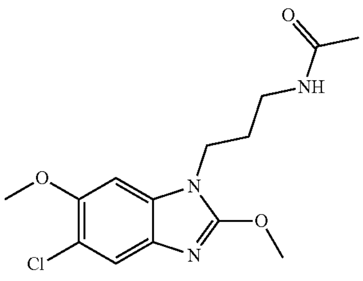

$^{1}H$ NMR (400 MHz, $CDCl_3$) δ 1.48 (t, J=7.0 Hz, 3H), 1.94-2.01 (m, 5H), 3.24 (q, J=4.80 Hz, 2H), 3.92 (s, 3H), 3.99 (t, J=6.8 Hz, 2H), 4.57 (q, J=6.8 Hz, 2H), 5.58 (br s, 1H), 6.71 (s, 1H), 7.52 (s, 1H). $^{13}C$ NMR (125 MHz, $CDCl_3$) δ ppm 14.74; 23.28; 28.73; 36.91; 39.70; 57.11; 66.48; 93.25; 116.79; 119.10; 132.35; 134.10; 150.67; 157.06; 170.22. MS (ESI) m/z calculated $C_{15}H_{20}ClN_3O_3$: 325.1193; found [M+H]+ 326.1292

In the HFD model, animals were initially maintained on a HFD for 4 weeks to induce a significant body weight (BW) gain before treatment was initiated. Animals on the HFD were then orally treated once daily with compound of formula I at 10 and 30 mg/kg, compound of formula II at 10 and 30 mg/kg or dapagliflozin at 5 mg/kg for 9 weeks. Two vehicle-treated control groups, fed either normal chow (Chow Vehicle) or HFD (HFD Vehicle), were also included.

BW and food intake (FI) were assessed during the study and the results are displayed in FIG. 1. Animals from the HFD Vehicle steadily increased their BW from a starting average of 459.9 g on day 1 to 612.4 g on day 57. Interestingly, the treatment with compound of formula I (10 and 30 mg/kg p.o.) significantly reduced body weight (BW) on days 13 to 32 ($p<0.05$) and dapagliflozin (5 mg/kg p.o.) on days 2 to 48, 50 to 54 and 56 ($p<0.05$) compared with HFD Vehicle animals (FIG. 1A). A trend towards reduced BW gain from day 1 to 57 (FIG. 1C) was also observed for animals treated with compound I at 10 and 30 mg/kg p.o. ($p=0.098$) and dapagliflozin at 5 mg/kg p.o. ($p=0.051$), when compared with HFD Vehicle. In contrast, the treatment with compound of formula II (10 and 30 mg/kg) had no significant effects on daily BW gain. Compound I and compound II did not affect daily food intake compared with HFD Vehicle group, apart from isolated changes observed for the latter (FIGS. 1B and 1D). Conversely, dapagliflozin significantly increased daily FI from day 8 to 56 ($p<0.05$) and the average daily FI ($p<0.001$) compared to HFD Vehicle.

The degree of insulin resistance and glucose intolerance were assessed using the Homeostatic Model Assessment for Insulin Resistance (HOMA-IR) method (van Dijk T H et al. (2013). A novel approach to monitor glucose metabolism using stable isotopically labelled glucose in longitudinal studies in mice. Lab Anim. 47(2):79-88.). HOMA-IR was calculated based on the plasma insulin and glucose concentrations on day 51 after a 4-hour fast. HFD Vehicle animals had significantly increased plasma glucose (+17.6%, $p<0.01$), insulin (+56.4%, $p<0.05$) and HOMA-IR (+79.3%, $p<0.01$) when compared to the Chow Vehicle group (FIG. 2). As expected, dapagliflozin significantly decreased plasma glucose (−21.6% $p<0.001$), plasma insulin (−56.7%, $p<0.001$) and plasma HOMA-IR (−66.7%, $p<0.001$) when compared to HFD Vehicle. Notably, compound of formula I also significantly reduced plasma glucose at the 10 mg/kg p.o. dose (−16.4%, $p<0.01$). At the highest dose (30 mg/kg p.o.), compound I according to the present invention significantly reduced both plasma glucose (−17%, $p<0.01$) and HOMA-IR (−36%, $p<0.01$) compared with HFD Vehicle (FIGS. 2A and 2C). In contrast, the comparative compound (compound II) did not alter plasma glucose, insulin or HOMA-IR when compared to HFD Vehicle.

The effects on body composition and on the weight of selected tissues (brown fat pad, epididymal fat pad, liver or gastrocnemius muscle) were assessed after the study was terminated (days 65/66). The weights of tissues were analyzed in two ways: i) BW on day 1 was used as a covariate to correct for differences in the BW at the start of the study or ii) the terminal BW (days 65/66) was used as a covariate to correct for changes due to weight loss (Table 3). Dapagliflozin led to a significant increase in liver weight compared to HFD Vehicle when data was corrected for the terminal BW (+10.8%, p<0.01). Conversely, a trend toward liver weight reduction was seen for both groups of the benzimidazole derivative of formula I treated animals in the analysis corrected by the initial BW (p=0.12). Apart from these changes, no significant effect on the weight of the selected tissues was observed in comparisons against the HFD Vehicle group, irrespective of the correction. Body composition was determined using FoodScan™ near-infrared analyzer analysis, which assessed water, protein and fat content and the final carcass weight (Table 4). No effect of benzimidazole derivative of formula I according to the present invention or comparative compound II was seen in any of the parameters evaluated in comparisons against the HFD Vehicle control. Dapagliflozin significantly reduced final carcass weight compared to HFD Vehicle (p<0.05), but the body composition was not altered.

As only the benzimidazole derivative of formula I according to the present invention, but not the comparative benzimidazole compound II, impacted BW gain, liver weight, plasma glucose levels and HOMA-IR in the HFD model, specific effects of compound I in the liver of the animals were evaluated in comparison with dapagliflozin and control groups. HFD Vehicle animals exhibited markedly increased liver triglyceride content and concentration (+473% and +409%, respectively) compared to the Chow Vehicle control (FIGS. 3A and 3B). Interestingly, treatments with compound of formula I (10 and 30 mg/kg p.o.) significantly reduced the liver triglyceride content (−41.3% and −55.1%, respectively, p<0.05) and compound I at 30 mg/kg p.o. significantly reduced the liver triglyceride concentration by 51.6% (p<0.01) compared to HFD Vehicle. In contrast, dapagliflozin treatment did not significantly reduce hepatic triglyceride content, nor concentration when compared to the HFD Vehicle control. Liver glycogen content and concentration were similar in both the Chow Vehicle and HFD Vehicle animals (FIGS. 3C and 3D). The compound of formula I (10 and 30 mg/kg p.o.) significantly (p<0.05) reduced liver glycogen content (by 36.6% and 36.6% respectively) and concentration (by 42.8% and 40.8%, respectively) when compared to HFD Vehicle. No effect of dapagliflozin was observed on liver glycogen content or concentration compared to the HFD Vehicle control.

Liver was also assessed for NAFLD by histopathological analysis (FIGS. 3E-H). Samples were sectioned, stained and scored following a method previously described (Kleiner D E et al. (2005). Design and validation of a histological scoring system for nonalcoholic fatty liver disease. Hepatology. 41(6):1313-21; Nishida T et al. (2013). Spontaneous onset of nonalcoholic steatohepatitis and hepatocellular carcinoma in a mouse model of metabolic syndrome. Lab Invest. 93(2):230-41). The parameters analyzed were: steatosis (0-3), lobular inflammation (0-3) and hepatocellular ballooning (0-2). The total "NAFLD activity score" (NAS) score was calculated as the sum of all parameters (0-8). The liver of Chow Vehicle animals had no pathology scores (zero) for steatosis, lobular inflammation, hepatocellular ballooning and no score for total NAS. Pathology scores for steatosis, lobular inflammation and total NAS were significantly (p<0.05) increased in the HFD Vehicle group, whereas hepatocellular ballooning was not significantly affected. Remarkably, the benzimidazole derivative of formula I according to the present invention (30 mg/kg p.o.) significantly (p<0.05) reduced steatosis by −57% when compared to the HFD group (FIG. 3F). Lobular inflammation was also reduced in animals treated with the benzimidazole derivative of formula I according to the present invention at the 30 mg/kg dose, such that it was no longer significantly different from the Chow Vehicle control (FIG. 3G). A trend toward significance was also observed for the total NAS value between this group and the HFD Vehicle animals (FIG. 3E, p=0.126). Conversely, no effect on the evaluated parameters was observed for dapagliflozin-treated rats in comparison with the HFD Vehicle group.

TABLE 1

In vitro pharmacology of benzimidazole derivative of formula I at MT1 and MT2 receptors in comparison with melatonin and the compound of formula II

| Compound | MT1 agonism EC50 (nM) [I.A. (%)] | MT2 agonism EC50 (nM) [I.A. (%)] |
|---|---|---|
| Melatonin | 0.11 [100] | 0.07 [100] |
| Benzimidazole derivative of formula I | 0.25 [100] | 2.8 [101] |
| Comparative compound of formula II | 3.4 [121] | 0.39 [105] |

Cellular functional assays were performed in the agonist mode.
EC50—half-maximal effective concentration.
I.A.—Intrinsic activity.

TABLE 2

Plasma and brain exposure and brain-to-plasma ratio in Wistar and Sprague Dawley (SD) rats for the compound of formula I and the compound of formula II

| Species | Time | Plasma concentration (μg/mL) ∣ Brain concentration (μg/g) ∣ Brain-to-plasma ratio | |
|---|---|---|---|
| (Dose) | (h) | Compound of formula I | Compound of formula II |
| Wistar Han | 0.37 | 30.53 ∣ 6.39 ∣ 0.20 | 54.50 ∣ 4.40 ∣ 0.08 |
| (100 mg/kg) | 2 | 45.37 ∣ 9.42 ∣ 0.21 | 48.00 ∣ 4.88 ∣ 0.10 |
| | 6 | 30.63 ∣ 4.65 ∣ 0.15 | 39.33 ∣ 3.62 ∣ 0.09 |
| SD | 0.5 | 4.00 ∣ 0.37 ∣ 0.09 | 14.75 ∣ 0.92 ∣ 0.06 |
| (10 mg/kg) | 2 | 0.24 ∣ 0.03 ∣ 0.11 | 2.08 ∣ 0.08 ∣ 0.04 |
| | 8 | ND ∣ ND ∣ ND | 0.004 ∣ ND ∣ ND |
| SD | 0.5 | 17.55 ∣ 1.82 ∣ 0.11 | 35.40 ∣ 2.02 ∣ 0.06 |
| (30 mg/kg) | 2 | 7.71 ∣ 0.91 ∣ 0.12 | 24.75 ∣ 1.23 ∣ 0.05 |
| | 8 | 0.01 ∣ ND ∣ ND | 0.71 ∣ 0.03 ∣ 0.05 |

Mean data of 2-3 animals per timepoint. Compounds were administered p.o. to Wistar (100 mg/kg) and Sprague Dawley (SD) rats (10 and 30 mg/kg) and samples (plasma and brain) were collected at selected timepoints.
ND—Not determined due to brain concentration below the lower limit of quantification (5 ng/g).

TABLE 3

Effect of compound of formula I and the comparative compound of formula II on tissues of male SD rats maintained on HFD

| Group | Data adjustment | Brown adipose tissue | Epididymal fat pads | Liver | Gastrocnemius |
|---|---|---|---|---|---|
| HFD Vehicle | day 1 | 0.678 ± 0.053 | 13.5 ± 1.1 | 19.9 ± 0.8 | 3.45 ± 0.10 |
| Dapagliflozin at 5 mg/kg | | 0.679 ± 0.047 | 12.2 ± 0.7 | 20.9 ± 0.5 | 3.34 ± 0.09 |

TABLE 3-continued

Effect of compound of formula I and the comparative compound of formula II on tissues of male SD rats maintained on HFD

| Group | Data adjustment | Brown adipose tissue | Epididymal fat pads | Liver | Gastrocnemius |
|---|---|---|---|---|---|
| Compound of formula I at 10 mg/kg | | 0.700 ± 0.091 | 13.1 ± 1.5 | 17.7 ± 0.8 # | 3.30 ± 0.14 |
| Compound of formula I at 30 mg/kg | | 0.801 ± 0.066 | 13.9 ± 1.0 | 18.6 ± 0.9 # | 3.35 ± 0.10 |
| Compound of formula II at 10 mg/kg | | 0.767 ± 0.067 | 13.8 ± 1.6 | 18.4 ± 0.7 | 3.21 ± 0.12 |
| Compound of formula II at 30 mg/kg | | 0.751 ± 0.076 | 13.2 ± 0.8 | 20.5 ± 0.6 | 3.39 ± 0.09 |
| HFD Vehicle | day 65/66 | 0.668 ± 0.052 | 13.0 ± 1.0 | 19.5 ± 0.8 | 3.43 ± 0.10 |
| Dapagliflozin at 5 mg/kg | | 0.697 ± 0.050 | 13.0 ± 0.7 | 21.6 ± 0.3 * | 3.37 ± 0.09 |
| Compound of formula I at 10 mg/kg | | 0.719 ± 0.084 | 13.9 ± 1.1 | 18.5 ± 0.5 | 3.32 ± 0.15 |
| Compound of formula I at 30 mg/kg | | 0.808 ± 0.062 | 14.2 ± 1.2 | 18.9 ± 0.5 | 3.36 ± 0.10 |
| Compound of formula II at 10 mg/kg | | 0.760 ± 0.068 | 13.5 ± 1.6 | 18.2 ± 0.7 | 3.21 ± 0.13 |
| Compound of formula II at 30 mg/kg | | 0.741 ± 0.076 | 12.8 ± 0.8 | 20.1 ± 0.5 | 3.37 ± 0.09 |

Data is shown as mean ± SEM (n = 9-10). Means were adjusted for BW differences between the treatment groups on day 1 or days 65/66 (study termination). SEM was calculated from the residuals of the statistical model. Compound of formula I, compound of formula II, dapagliflozin and vehicle were administered to animals fed normal chow or HFD and parameters were assessed after termination. Data was analyzed by ANCOVA with treatment and cohort as factors and BW on day 1 or final carcass weight as covariates (for data adjustment for BW on day 1 or day 65/66, respectively). Treatment groups were compared with HFD Vehicle by separate Williams' tests (Compound I and compound II) or multiple t tests (dapagliflozin) and statistically significant differences are denoted by ** ($p < 0.01$).

($p = 0.12$) means a trend toward significance in comparison with HFD Vehicle.

TABLE 4

Effect of the benzimidazole derivative of formula I and the comparative compound of formula II on body composition of male SD rats maintained on HFD

| Group | Final carcass weight (g) | Water (%) | Fat (%) | Protein (%) |
|---|---|---|---|---|
| HFD Vehicle | 591.9 ± 3.7 †† | 57.2 ± 0.9 † | 19.3 ± 1.2 †† | 19.5 ± 0.3 †† |
| Dapagliflozin at 5 mg/kg | 564.5 ± 9.4 * † | 58.9 ± 1.0 | 16.8 ± 1.3 | 20.6 ± 0.4 |
| Compound I at 10 mg/kg | 561.7 ± 13.0 | 56.1 ± 1.2 † | 20.5 ± 1.5 † | 19.7 ± 0.4 |
| Compound I at 30 mg/kg | 584.0 ± 13.6 | 56.5 ± 1.4 † | 20.0 ± 1.7 † | 19.6 ± 0.5 † |
| Compound II at 10 mg/kg | 587.6 ± 6.3 † | 56.0 ± 1.8 † | 20.8 ± 2.3 †† | 19.2 ± 0.6 †† |
| Compound II at 30 mg/kg | 593.3 ± 11.4 †† | 58.4 ± 1.9 | 17.9 ± 2.3 † | 19.8 ± 0.5 |

Data is shown as adjusted means ± SEM (n = 9-10). SEM was calculated from the residuals of the statistical model. Analysis was by robust regression of data with treatment as a factor and BW on day 1 as a covariate. Treatment groups were compared to HFD Vehicle by separate Williams' tests (Compound I and compound II) or multiple t tests (dapagliflozin) and statistically significant differences are denoted by * ($p < 0.05$). Comparisons against Chow Vehicle were by multiple t tests (HFD Vehicle and dapagliflozin groups) or Dunnett's test (Compound I and compound II) and statistically significant differences are denoted by † ($p < 0.05$) and †† ($p < 0.01$).

The invention claimed is:

1. A method for the treatment of a metabolic disorder selected from the group consisting of obesity, diabetes, non-alcoholic fatty liver disease and non-alcoholic steatohepatitis comprising administering a benzimidazole compound of formula I:

Formula I

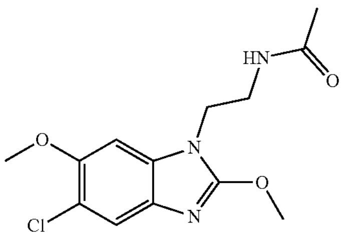

or pharmaceutically acceptable salts, crystals, hydrates, solvates, prodrugs or metabolites thereof, to a patient.

2. The method according to claim 1, wherein 0.01 to 5000 mg of the benzimidazole compound of formula I is administered to the patient.

3. The method according to claim 1 wherein the pharmaceutically acceptable salts of the benzimidazole compound of formula I comprise a salt selected from the group consisting of:

(a) inorganic addition salts selected from the group consisting of hydrochloride, hydrobromide, sulfate, nitrate, and phosphate;

(b) organic addition salts selected from the group consisting of acetate, propionate, hexanoate, heptanoate, glycolate, piruvate, lactate, malonate, malate, maleate, fumarate, tartrate, citrate, succinate, mesylate, acistrate, besylate, tosylate, xinafoate, benzoate, p-toluenesulfonate, cinnamate, p-chlorobenzenesulfonate, 2-naphtalenesulfonate, p-toluenesulphonate, camphorsulfonate, trimethylacetate, t-butylacetate, laurylsulphate, gluconate, glutarate, hydroxynaphthoate, salicylate, stearate, muconate, mandelate, and 2-hydroxyethanesulfonate;

(c) alkaline addition salts of metals selected from the group consisting of sodium, potassium, lithium, calcium, magnesium, bismuth, and bromide; and (d) pharmaceutically acceptable salts with organic bases selected from the group consisting of primary, secondary and tertiary amines; or salts with an amino acid selected from the group consisting of arginine, lysine, histidine, caffeine, procaine, hydrobamine, choline, betaine, ethylenediamine, glycosamine, teobromine, purine, and morpholine.

4. The method according to claim 1 wherein the benzimidazole compound is administered in the form of a pharmaceutical composition comprising the benzimidazole compound of formula I and a pharmaceutically acceptable excipient.

* * * * *